United States Patent [19]

Pinchuk

[11] Patent Number: 5,229,431

[45] Date of Patent: Jul. 20, 1993

[54] CRACK-RESISTANT POLYCARBONATE URETHANE POLYMER PROSTHESES AND THE LIKE

[75] Inventor: Leonard Pinchuk, Miami, Fla.

[73] Assignee: Corvita Corporation, Miami, Fla.

[21] Appl. No.: 918,356

[22] Filed: Jul. 23, 1992

Related U.S. Application Data

[63] Continuation of Ser. No. 794,621, Nov. 14, 1991, Pat. No. 5,133,742, which is a continuation of Ser. No. 538,986, Jun. 15, 1990, abandoned.

[51] Int. Cl.$^5$ .............................. C08G 18/14
[52] U.S. Cl. .................................. 521/159; 521/163; 521/164; 521/172; 521/173; 528/59; 528/61; 528/65; 528/66; 623/66
[58] Field of Search ............... 521/159, 163, 164, 172, 521/173; 528/59, 65, 66, 61; 623/66

[56] References Cited

U.S. PATENT DOCUMENTS

| | | | |
|---|---|---|---|
| 3,867,350 | 4/1973 | Pedain et al. | 260/77.5 |
| 4,024,113 | 5/1977 | Ammons | 260/77.5 |
| 4,131,731 | 12/1978 | Lai et al. | 528/370 |
| 4,160,853 | 7/1979 | Ammons | 528/85 |
| 4,456,745 | 6/1984 | Rajan | 528/85 |
| 4,475,972 | 10/1984 | Wong | 623/1 |
| 4,501,873 | 2/1985 | Rasshofer | 528/85 |
| 4,738,740 | 4/1988 | Pinchuk et al. | 156/167 |
| 4,739,013 | 4/1988 | Pinchuk | 525/101 |
| 4,769,030 | 9/1988 | Pinchuk | 623/1 |
| 4,810,749 | 3/1989 | Pinchuk | 524/730 |
| 4,851,009 | 7/1989 | Pinchuk | 623/66 |
| 4,882,148 | 11/1989 | Pinchuk | 424/423 |
| 5,109,077 | 4/1992 | Wick | 525/467 |

FOREIGN PATENT DOCUMENTS 2715566 12/1978 Fed. Rep. of Germany.

OTHER PUBLICATIONS

I.C.I. Publication, "Polyurethane Emulsions Aliphatic", *Permuthane Coatings.*
I.C.I. Publication, "Two Component Urethanes, Pre-Polymers, Polyols and Diols," *Permuthane Coatings.*

*Primary Examiner*—Maurice J. Welsh
*Attorney, Agent, or Firm*—Lockwood, Alex, Fitzgibbon & Cummings

[57] ABSTRACT

An especially crack-resistant yet elastomeric and pliable polyurethane is provided as a polymer which is especially suitable for medical prosthesis, implants, roofing insulators and the like. The polymer is a polycarbonate urethane polymer which is substantially completely devoid of ether linkages.

38 Claims, 2 Drawing Sheets

CRACK-RESISTANT POLYCARBONATE URETHANE POLYMER PROSTHESES AND THE LIKE

This application is a continuation, of copending application Ser. No. 749,621, filed Nov. 14, 1991, U.S. Pat. No. 5,133,742, which is a continuation of application Ser. No. 538,986, filed Jun. 15, 1990, abandoned.

BACKGROUND AND DESCRIPTION OF THE INVENTION

The present invention generally relates to implantable prosthesis and the like and to methods for making or treating same in order to substantially prevent cracking or crazing thereof when they are implanted or otherwise subjected to degradation conditions. A medical prosthesis or the like according to this invention includes a polycarbonate urethane polymeric surface which will not crack or degrade when subjected to implantation for substantial time periods during which other types of polyurethane surfaces would crack or degrade.

Several biocompatible materials which are quite suitable for use in making implantable medical devices that may be broadly characterized as implantable prostheses exhibit properties that are sought after in such devices, including one or more of exceptional biocompatibility, extrudability, moldability, good fiber forming properties, tensile strength, elasticity, durability and the like. However, some of these otherwise highly desirable materials exhibit a serious deficiency when implanted within the human body or otherwise subjected to harsh environments, such deficiency typically being manifested by the development of strength-reducing and unsightly cracks. For example, surface fissuring or cracking occurs after substantial exposure, which may be on the order of one month or more or shorter time periods depending upon the materials and the implant conditions and exposure to body fluids and cells such as are encountered during in vivo implantation and use. Many implantable prostheses are intended to be permanent in nature and should not develop any substantial degradation or cracking during years of implantation.

Several theories have been promulgated in attempting to define the cause of this cracking phenomenon. Proposed mechanisms include oxidative degradation, hydrolytic instability, enzymatic destruction, thermal and mechanical failure, immunochemical mechanisms, inhibition of lipids and combinations of the above. Prior attempts to control surface fissuring or cracking upon implantation or the like include incorporating antioxidants within a biocompatible polymer and subjecting the biocompatible polymer to various different annealing conditions, typically including attempting to remove stresses within the polymer by application of various heating and cooling conditions. Attempts such as these have been largely unsuccessful.

Other treatment approaches have been utilized, or attempted, to increase the structural stability of especially desirable materials. Included in the biocompatible materials which are desirable from many points of view but which exhibit a marked tendency to crack or degrade over time are the polyurethane materials and other biocompatible polymers that are of an elastomeric nature. It is particularly advantageous to use these types of materials for making products in respect of which compliance and/or flexibility, high tensile strength and excellent fatigue life can be desirable features. One basic approach which has been taken heretofore in order to render these materials more suitable for implantation and other applications where material degradation can develop has been to treat the materials with so-called crack preventatives. Exemplary approaches in this regard are found in U.S. Pat. Nos. 4,769,030, 4,851,009 and 4,882,148, the subject matter thereof being incorporated by reference hereinto. Treatments, of course, require additional procedures and components, thereby somewhat complicating manufacturing procedures, and it would be advantageous if the material out of which the product is made would itself have the desired properties. It is also advantageous for the material to be compatible with other materials that are commonly used in the medical fields such as with adhesives, surface coatings and the like.

An especially difficult problem in this regard is experienced when attempting to form prostheses with procedures including the extrusion or spinning of polymeric fibers, such as are involved in winding fiber-forming polymers into porous vascular grafts or similar products, for example as described in U.S. Pat. No. 4,475,972, the subject matter thereof being incorporated by reference hereinto. Such vascular grafts or the like include a plurality of strands that are of a somewhat fine diameter size such that, when cracking develops after implantation, this cracking often manifests itself in the form of complete severance of various strands of the device. Such strand severance cannot be tolerated to any substantial degree and still hope to provide a device that can be successfully implanted or installed on a generally permanent basis whereby the device remains viable for a number of years.

Numerous polymeric structures such as vascular grafts made from spun fibers appear to perform very satisfactorily insofar as their viability when subjected to physical stress conditions is concerned, for example conditions which approximate those experienced during and after implantation, including stresses imparted by sutures, other fastening members and the like. For example, certain polyurethane fibers, when subjected to constant stress under in vitro conditions, such as in saline solution at body temperatures, do not demonstrate cracking that is evident when substantially the same polyurethane spun fibers are subjected to in vivo conditions. Accordingly, while many materials, such as certain various polyurethanes, polypropylenes, polymethylmethacrylates and the like, may appear to provide superior medical devices or prostheses when subjected to stresses under in vitro conditions, they are found to be less than satisfactory when subjected to substantially the same types of stresses but under in vivo conditions.

There is accordingly a need for a material which will not experience surface fissuring or cracking under implanted or in vivo conditions and which is otherwise desirable and advantageous as a material for medical devices or prostheses that must successfully delay, if not eliminate, the cracking phenomenon even after implantation for months and years, in many cases a substantial number of years. In addition, other products which are not necessarily intended for medical use can benefit from their being made of such a non-cracking material. Products in this regard could include those subjected to harsh environmental conditions such as weathering and the like. Exemplary medical devices or prostheses for which such a non-cracking material would especially advantageous include vascular grafts, compliant sutures, breast implants, heart leaflet valves, pacemaker lead insulators, intraocular lens loops or haptics, diaphragms for artificial hearts, tubing for infusion pumps, artificial ligaments, artificial skin, drug eluting matrices, lattices for cell seeding and artificial organs, and the like. Examples of non-medical applications of these urethanes include urethane for roofing insulators, sewer gaskets, industrial tubing and the like.

In summary, the present invention achieves these types of objectives by providing a polycarbonate urethane polymer as the material out of which crack-resistant products are made. The polycarbonate urethane polymer is exceptionally crack-resistant, even under in vivo conditions. The polymeric backbone has recurring urethane and/or urea groups, and the polymer is a reaction product of at least a polycarbonate glycol having terminal hydroxyl groups and a diisocyanate having terminal isocyanate groups. A chain extender having terminal hydroxyl or amine groups may or may not be added. It is especially preferred that the resultant hardness of the polycarbonate urethane be at least as hard as about Shore 70A, preferably between about Shore 80A and Shore 75D.

It is accordingly a general object of the present invention to provide improved crack-resistant devices and products.

Another object of this invention is to provide a polymeric material and products made therefrom which are particularly resistant to degradation, even under in vivo conditions.

Another object of the present invention is to provide an improved polyurethane type of material which can be spun through a spinnerette or extruded through and/or into suitable molding devices into products which exhibit superior crack-resistant properties.

Another object of this invention is to provide improved implantable devices and/or prostheses which exhibit an exceptional ability to prevent the formation of cracks and strand severances upon implantation for substantial time periods such as those needed for generally permanent implantation procedures.

Another object of the present invention is to provide an improved vascular graft and the like that is made from spun fibers of polycarbonate urethane polymer and that exhibits exceptional stability with respect to crack formation and strand severance development under in vivo conditions.

Another object of the present invention is to provide an improved extruded device or product that is unusually crack-resistant, even when subjected to harsh environmental conditions.

Another object of the present invention is to provide improved cast polymer products including a polycarbonate urethane polymer which exhibits exceptional crack-resistance.

These and other objects, features and advantages of the present invention will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
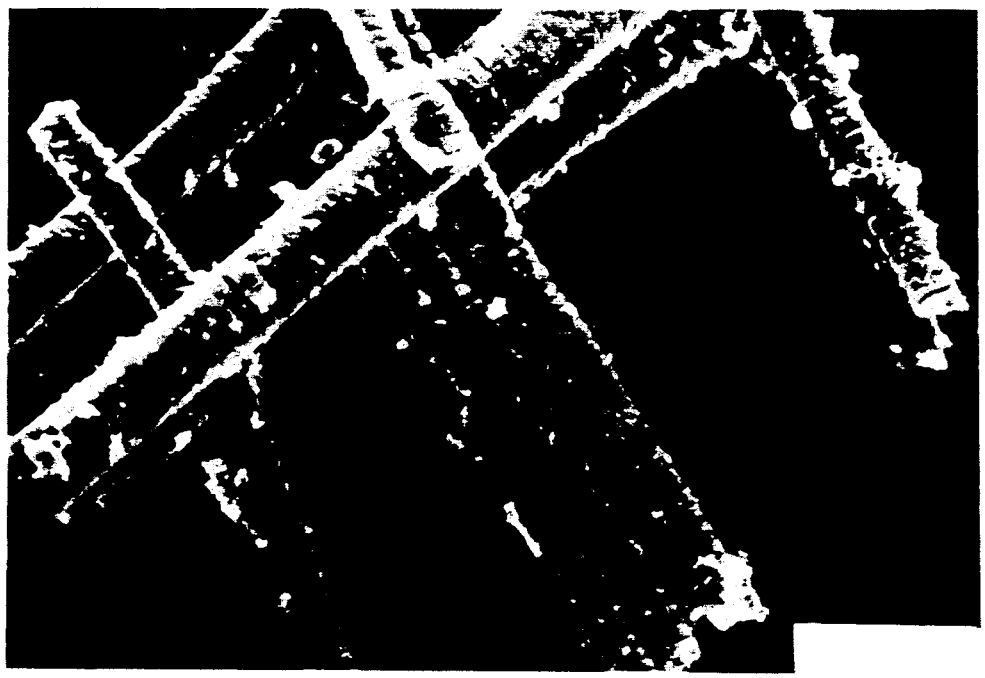
FIG. 1 is a photomicrograph of a section of a vascular graft made by spinning a polyether urethane polymer not in accordance with this invention and after subcutaneous implantation, explantation and cleaning.

Generally known polyurethanes include those specified in U.S. Pat. Nos. 4,739,013 and 4,810,749, the subject matter thereof being incorporated by reference hereinto. As discussed in those patents and elsewhere, the term polyurethane encompasses a family of polymers that usually include three principle components. These are: a macroglycol, a diisocyanate and a chain extender. They are generally classified as polyurethanes inasmuch as the backbone thereof includes urethane groups and often also urea groups, which groups are recurring units within the polymer backbone.

Formation of a typical polyurethane includes reacting an —OH or hydroxyl group of the macroglycol component with an —NCO or isocyanate group of the diisocyanate component. A further linkage site reacts another terminal —NCO or isocyanate group of the diisocyanate reactant with a terminal hydroxyl (or amine) group of the chain extender. It can be appreciated that a polyurethane can also be synthesized with a macroglycol and isocyanate only; however, typical urethanes that are commercially available include a chain extender.

The polymerization typically will be carried out in the presence of a suitable solvent and under appropriate reaction conditions, although non-solvent reactions could be carried out, especially if the polymer is not to be extruded into fibers but is, for example, to be formed into pellets or the like for other extrusion and/or molding procedures, or is to be made into foams.

With particular reference to the macroglycol component of polyurethanes in general, three primary families of macroglycols are available commercially at the present time. These are the polyester glycols, the polyether glycols and the polycarbonate glycols. Also available are a family of macroglycols that are amine terminated rather than hydroxyl terminated. The polyester glycols are by far the most widely used macroglycols for polyurethanes at the present time. These are generally known to be unsuitable for many applications such as long-term medical implantation applications, for the principal reason that polyurethanes of this type are generally easily hydrolyzed because the ester linkages thereof are easily cleaved by water molecules which would, of course, be present in numerous applications including various medical uses.

Polyether urethanes have had some success and are fairly widely used in medical applications. Polyether urethanes are known to be degraded by cellular components and metal ions and will not survive the rigors of a physiological environment, requiring the application of treatments thereto in order to prevent biodegradation. This is especially true when the polyether urethane is made into devices having thin or fine structures or portions. Polycarbonate urethanes are typically more expensive and difficult to process and currently are not in wide use. Other classes of polyurethanes could be prepared by using other macroglycols, such as polyolefin glycol, a polyesteramide glycol, a polycaprolactone glycol, an amine terminated macroglycol or a polyacrylate glycol. Similarly, polyols having a functionality greater than 2 can be used.

In accordance with the present invention, the macroglycol is a polycarvonate glycol. A process for preparing polycarbonate glycols which are linear polycarbonates having terminal hydroxyl groups is described in U.S. Pat. No. 4,131,731, the subject matter thereof being incorporated by reference hereinto.

A polycarbonate component is characterized by repeating

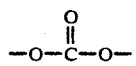

units, and a general formula for a polycarbonate macroglycol is as follows

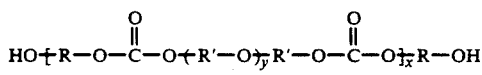

wherein x is from 2 to 35, y is 0, 1 or 2, R either is cycloaliphatic, aromatic or aliphatic having from about 4 to about 40 carbon atoms or is alkoxy having from about 2 to about 20 carbon atoms, and wherein R' has from about 2 to about 4 linear carbon atoms with or without additional pendant carbon groups.

Examples of typical aromatic polycarbonate macroglycols include those derived from phosgene and bisphenol A or by ester exchange between bisphenol A and diphenyl carbonate such as (4,4'-dihydroxy-diphenyl-2,2'-propane) shown below, wherein n is between about 1 and about 12.

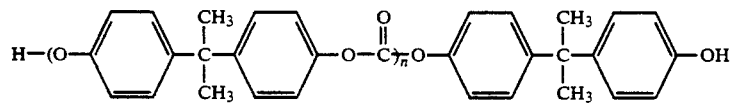

Typical aliphatic polycarbonates are formed by reacting cycloaliphatic or aliphatic diols with alkylene carbonates as shown by the general reaction below:

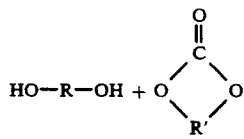

wherein R is cyclic or linear and has between about 1 and about 40 carbon atoms and wherein R' is linear and has between about 1 and about 4 carbon atoms.

Typical examples of aliphatic polycarbonate diols include the reaction products of 1,6-hexanediol with ethylene carbonate, 1,4-butanediol with propylene carbonate, 1,5-pentanediol with ethylene carbonate, cyclohexanedimethanol with ethylene carbonate and the like and mixtures of the above such as diethyleneglycol and cyclohexanedimethanol with ethylene carbonate.

When desired, polycarbonates such as these can be copolymerized with components such as hindered polyesters, for example phthalic acid, in order to form carbonate/ester copolymer macroglycols. Copolymers formed in this manner can be entirely aliphatic, entirely aromatic, or mixed aliphatic and aromatic. The polycarbonate macroglycols typically have a molecular weight of between about 200 and about 4000 Daltons.

Diisocyanate reactants according to this invention have the general structure OCN—R'—NCO, wherein R' is a hydrocarbon that may include aromatic or non-aromatic structures, including aliphatic and cycloaliphatic structures. Exemplary isocyanates include the preferred methylene diisocyanate (MDI), or 4,4-methylene bisphenyl isocyanate, or 4,4'-diphenylmethane diisocyanate and hydrogenated methylene diisocyanate (HMDI). Other exemplary isocyanates include hexamethylene diisocyanate and the toluene diisocyanates such as 2,4-toluene diisocyanate and 2,6-toluene diisocyanate, 4,4'tolidine diisocyanate, m-phenylene diisocyanate, 4-chloro-1,3-phenylene diisocyanate, 4,4-tetramethylene diisocyanate, 1,6-hexamethylene diisocyanate, 1,10-decamethylene diisocyanate, 1,4-cyclohexylene diisocyanate, 4,4'-methylene bis (cyclohexylisocyanate), 1,4-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates appliable to this invention are specialty isocyanates containing sulfonated groups for improved hemocompatibility and the like.

Suitable chain extenders included in the polymerization of the polycarbonate urethanes should have a functionality that is equal to or greater than two. A preferred and well-recognized chain extender is 1,4-butanediol. Generally speaking, most diols or diamines are suitable, including the ethylenediols, the propylenediols, ethylenediamine, 1,4-butanediamine methylene dianiline heteromoleculs such as ethanolamine, reaction products of said diisocyanates with water, combination of the above, additional macroglycols and the like.

The polycarbonate urethane polymers according to the present invention should be substantially devoid of any significant ether linkages (i.e., when y is 0, 1 or 2 as represented in the general formula hereinabove for a polycarbonate macroglycol), and it is believed that ether linkages should not be present at levels in excess of impurity or side reaction concentrations. While not wishing to be bound by any specific theory, it is presently believed that ether linkages account for much of the degradation that is experienced by polymers not in accordance with the present invention because enzymes that are typically encountered in vivo, or otherwise, attack the ether linkage. Oxidation is experienced, and live cells probably catalyze degradation of these other polymers.

Because minimal quantities of ether linkages are unavoidable in the polycarbonate producing reaction, and because these ether linkages are suspect in the biodegradation of polyurethanes, the quantity of macroglycol should be minimized to thereby reduce the number of ether linkages in the polycarbonate urethane. In order to maintain the total number of equivalents of hydroxyl terminal groups approximately equal to the total number of equivalents of isocyanate terminal groups, minimizing the polycarbonate soft segment necessitates proportionally increasing the chain extender hard segment in the three component polyurethane system. Therefore, the ratio of equivalents of chain extender to macroglycol should be as high as possible. A consequence of increasing this ratio (i.e., increasing the amount of chain extender with respect to macroglycol) is an increase in hardness of the polyurethane. Typically, polycarbonate urethanes of hardnesses, measured on the Shore scale, less than 70A show small amounts of biodegradation. Polycarbonate urethanes of Shore 75A and greater show virtually no biodegradation.

The ratio of equivalents of chain extender to polycarbonate and the resultant hardness is a complex function that includes the chemical nature of the components of the urethane system and their relative proportions. However, in general, the hardness is a function of the molecular weight of both chain extender segment and polycarbonate segment and the ratio of equivalents thereof. Typically, for 4,4'-methylene bisphenyl diisocyanate (MDI) based systems, a 1,4-butanediol chain extender of molecular weight 90 and a polycarbonate urethane of molecular weight of approximately 2000 will require a ratio of equivalents of at least about 1.5 to 1 and no greater than about 12 to 1 to provide non-biodegrading polymers. Preferably, the ratio should be at least about 2 to 1 and less than about 6 to 1. For a similar system using a polycarbonate glycol segment of molecular weight of about 1000, the preferred ratio should be at least about 1 to 1 and no greater than about 3 to 1. A polycarbonate glycol having a molecular weight of about 500 would require a ratio in the range of about 1:2 to about 1.5:1.

The lower range of the preferred ratio of chain extender to macroglycol typically yields polyurethanes of Shore 80A hardness. The upper range of ratios typically yields polycarbonate urethanes on the order of Shore 75D. The preferred elastomeric and biostable polycarbonate urethanes for most medical devices would have a Shore hardness of approximately 85A.

Generally speaking, it is desirable to control somewhat the cross-linking that occurs during polymerization of the polycarbonate urethane polymer. A polymerized molecular weight of between about 80,000 and about 200,000 Daltons, for example on the order of about 120,000 Daltons (such molecular weights being determined by measurement according to the polystyrene standard), is desired so that the resultant polymer will have a viscosity at a solids content of 43% of between about 900,000 and about 1,800,000 centipoise, typically on the order of about 1,000,000 centipoise. Cross-linking can be controlled by avoiding an isocyanate-rich situation. Of course, the general relationship between the isocyanate groups and the total hydroxyl (and/or amine) groups of the reactants should be on the order of approximately 1 to 1. Cross-linking can be controlled by controlling the reaction temperatures and shading the molar ratios in a direction to be certain that the reactant charge is not isocyanate-rich; alternatively a termination reactant such as ethanol can be included in order to block excess isocyanate groups which could result in cross-linking which is greater than desired.

Concerning the preparation of the polycarbonate urethane polymers, they can be reacted in a single-stage reactant charge, or they can be reacted in multiple stages, preferably in two stages, with or without a catalyst and heat. Other components such as antioxidants, extrusion agents and the like can be included, although typically there would be a tendency and preference to exclude such additional components when a medical-grade polymer is being prepared.

Additionally, the polycarbonate urethane polymers can be polymerized in suitable solvents, typically polar organic solvents in order to ensure a complete and homogeneous reaction. Solvents include dimethylacetamide, dimethylformamide, dimethylsulfoxide toluene, xylene, m-pyrrol, tetrahydrofuran, cyclohexanone, 2-pyrrolidone, and the like, or combinations thereof.

While no treatment of the polycarbonate urethane polymer products according to this invention is required, suitable treatments can be conducted if desired. For example, they may be subjected to treatment with a crack preventative composition that includes an elastomeric silicone such as poly(dimethyl siloxane), as described in detail in U.S. Pat. No. 4,851,009. By this treatment, there is bonding between the product's substrate and the silicone polymer. Preferably, steps are taken in order to assist in directing the crack preventative into interstices or undulations of the device or product, and excesses should be removed by suitable means in order to avoid porosity reduction or other undesirable results due to residue or excess treatment material. Similarly, they can be surface grafted or coupled with drugs such as heparin, steroids, antibiotics and the like. The surface can be rendered more hemocompatible by sulfonation and the like.

EXAMPLE 1

A spinnable or castable polycarbonate urethane polymer was prepared in the following manner. The following reactants were charged into a vessel at 80° C. with constant mixing and with dimethylacetamide to prepare 1 kg of a 42.5% solids reaction product: 83.5 grams of methylene diisocyanate, 332.4 grams of polycarbonate diol (having a molecular weight of 1989), 7.5 grams of 1,4-butane diol chain extender, 1.5 grams of water, and 575 grams of dimethylacetamide. The reaction was continued for four hours, and the polycarbonate urethane polymer formed had a Shore hardness value of 60 A. The ratio of chain extender to polycarbonate soft segment was 1:1.

The resulting thick solution was spun through a spinnerette into a filamentous vascular graft, generally in accordance with the teachings of U.S. Pat. No. 4,475,972, the subject matter thereof being incorporated by reference hereinto. A more dilute solution can be used as a solvent cast system wherein the polymer solution is poured over a suitable mold in order to form products such as breast implants and heart leaflet valves.

EXAMPLE 2

A spinnable or castable polycarbonate urethane was prepared similar to that of Example 1; however, the ratio of chain extender to polycarbonate soft segment was increased from 1:1 to 2.5:1. The polymer was prepared at 42.5% solids content with 122.5 grams of MDI, 278.5 grams of polycarbonate diol of molecular weight 1989, 22.06 grams of 1,4-butanediol and 1.89 grams of water. The solvent was dimethylacetamide (575 grams). Castable films made from this formulation had a hardness of Shore 80 A.

EXAMPLE 3

A spinnable or castable polycarbonate urethane was prepared similar to that of Examples 1 and 2; however, the ratio of chain extender to polycarbonate soft segment was increased to 4:1. The polymer was prepared at 42.5% solids content with 156 grams of MDI, 248 grams of polycarbonate diol of molecular weight 1989, 45 grams of 1,4-butanediol and no water. The solvent was dimethylacetamide (550 grams). Castable films made from this formulation had a hardness of Shore 55 D.

EXAMPLE 4

An extrudable polycarbonate polyurethane was prepared by charging a reaction vessel at 60° C. with 283 grams of MDI and 644 grams of polycarbonate of molecular weight 1989. After approximately one hour, 73 grams of 1,4-butanediol was introduced to the reaction chamber and throughly mixed and subjected to a vacuum to remove evolving bubbles. The reaction was continued until solidification occured. The solid slab was annealed at 110° C. for 24 hours and then pelletized. Pellets formed in this manner are thermoplastic, Shore 80 A in hardness, and can be extruded at 180° C. to 220° C. into a product such as an insulating sheath for a pacemaker lead, or fibers for textile applications.

EXAMPLE 5

A spinnable or castable polycarbonate urethane was prepared similar to that of Example 1 with a ratio of chain extender to polycarbonate soft segment of 1:1, with a polycarbonate diol of molecular weight 940. The polycarbonate diol (276.5 grams) was reacted with 147 grams of MDI in 550 grams of DMA for one hour then chain extended with 26.5 grams of 1,4-butanediol. Castable films fabricated in the above manner had a Shore hardness of 80 A.

EXAMPLE 6

Vascular grafts of the filamentous type were formed by spinning onto a rotating mandrel in a manner generally described in U.S. Pat. No. 4,474,972 in order to form a plurality of filamentous vascular grafts. The grafts were implanted subcutaneously in an animal. After a period of implantation, the grafts were explanted, cleaned in a solution of 10% sodium hydroxide and 4% sodium hypochlorate for one hour, and then examined under a scanning electron microscope for evidence of fiber breakage and cracking.

FIG. 1 is a photomicrograph of a scanning electron microscopic reproduction of a typical untreated Shore 80 A polyether urethane polymer filamentous vascular graft which had been implanted for only four weeks. Severe cracking and strand breakage are evident, even though the grafts had been subjected to annealing conditions in an effort to reduce cracking and breakage.

Figure 2:
FIG. 2 is a photomicrograph of a section from a spun graft made from a polycarbonate urethane polymer, after subcutaneous implantation, explantation and cleaning.

Polycarbonate urethane polymer filamentous vascular grafts were, prior to implantation, placed under a tension condition by the following procedure. A one-inch long Delrin mandrel or rod was placed into a vascular graft, and opposite ends of the graft were stretched by an Instron machine to 70% of the ultimate tensile strength or elongation of the polycarbonate urethane polymer. The opposite ends were sutured in a "purse strings" manner around the mandrel in order to maintain the degree of stretch. The graft was removed from the Instron machine, and the implanting was conducted under this stretched condition. FIG. 2 is a photomicrograph of the scanning electron microscopic reproduction of a typical polycarbonate urethane polymer filamentous vascular graft which was explanted after 4 weeks. The particular polycarbonate urethane polymer was prepared from a reaction charge in which the ratio of soft segment polycarbonate diol equivalents to chain extender equivalents (hydroxyl groups) was 1 to 1 as in Example 1 to prepare a Shore 60 A polymer graft. Some cracking is evident.

Figure 3:
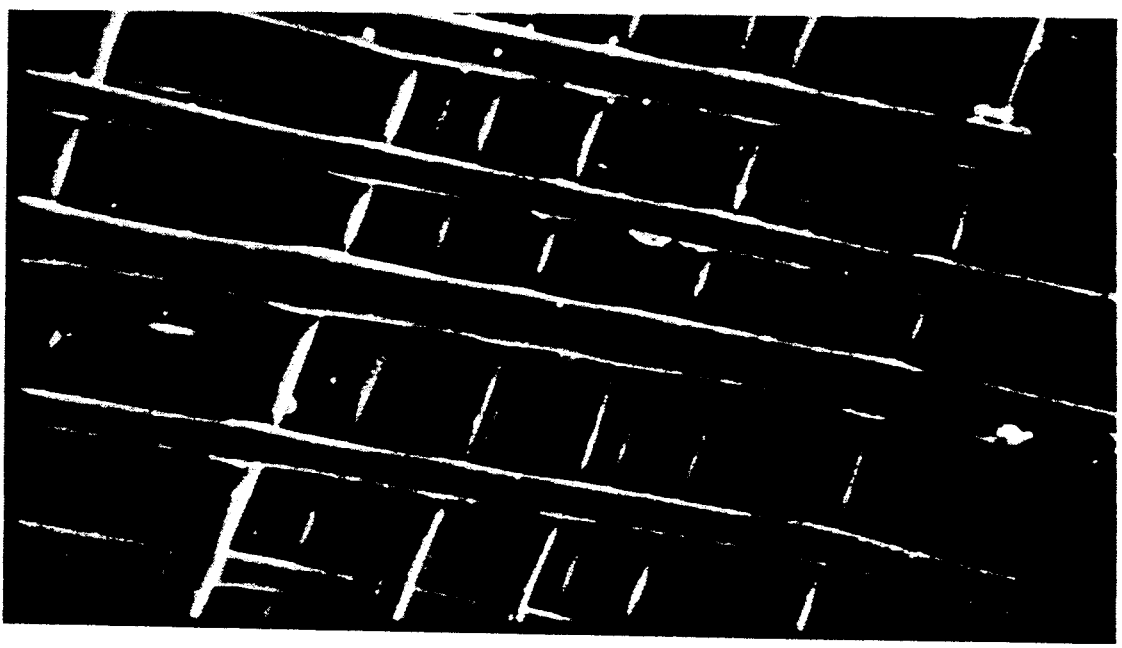
FIG. 3 is a photomicrograph of a section from a spun graft made from a polycarbonate urethane polymer formulated according to the present invention, also after subcutaneous implantation, explantation and cleaning.

FIG. 3 is a photomicrograph of the scanning electron microscopic image that is typical of an explanted polycarbonate urethane polymer of Shore 80 A (according to Example 2) filamentous graft which was implanted for six months. Fiber breakage is essentially non-existent, and no surface cracking can be seen. Here, the ratio of chain extender equivalents to polycarbonate equivalents was 2.5 to 1. Findings similar to this Example 2 result were also obtained for devices made with the polymers of Example 3, Example 4 and Example 5.

EXAMPLE 7

A soft polycarbonate foam was prepared by reacting 192 grams of polycarbonate diol of molecular weight 1818 with 119 grams of MDI. The reaction was continued for one hour at 60° C., after which 14 grams of 1,4-butanediol and 1.17 grams of water were added. The reaction continued until a soft, stable foam was produced.

EXAMPLE 8

A hard polycarbonate foam was prepared by reacting 151 grams of polycarbonate diol of molecular weight 1818 with 119 grams of MDI. The reaction was continued for one hour at 60° C., after which 21 grams of 1,4-butanediol and 2.52 grams of water were added. The reaction continued until a hard and durable foam was produced, which foam is suitable for use as a non-oxidizing roofing insulator.

It will be understood that the embodiments of the present invention which have been described are illustrative of some of the applications of the principles of the present invention. Numerous modifications may be made by those skilled in the art without departing from the true spirit and scope of the invention.

What is claimed is:

1. A non-biodegradable polycarbonate urethane polymer for forming crack-resistant implantable prostheses, the polymer comprising:
    a polymeric backbone having recurring groups selected from the group consisting of urethane groups, urea groups, carbonate groups and combinations thereof;
    said polymer being a reaction product of a reactant charge including: a polycarbonate glycol reactant having terminal hydroxyl groups, a diisocyanate reactant having terminal isocyanate groups, and a chain extender reactant having terminal hydroxyl or amine groups, wherein the polymer reaction product has a hardness in the range of about Shore 70A to about Shore 75D; wherein said polymeric backbone includes:
    a linkage site at which at least one of said terminal isocyanate groups of a diisocyanate reactant moiety had reacted with at least one of said terminal hydroxyl groups of a polycarbonate glycol reactant moiety;
    a linkage site at which another terminal isocyanate group of the diisocyanate reactant moiety had reacted with one of said terminal hydroxyl or amine groups of a polycarbonate glycol reactant moiety or a chain extender reactant moiety; and said polymer is substantially devoid of ether linkages, whereby the prostheses are crack-resistant when implanted, and cracking of the polymer is substantially prevented during in vivo implantation for in excess of six months.

2. The polymer according to claim 1, wherein the ratio of equivalents of chain extender to polycarbonate glycol is at least about 1.5 to 1.

3. The polymer according to claim 2, wherein said ratio of equivalents is between about 2 to 1 and about 4 to 1.

4. The polymer according to claim 2, wherein said polycarbonate glycol has a molecular weight of on the order of approximately 2000 Daltons, and said ratio of equivalents is at least about 2 to 1.

5. A polycarbonate urethane polymer for forming crack-resistant, durable foams, the polymer comprising:
   a polymeric backbone having recurring groups selected from the group consisting of urethane groups, urea groups, carbonate groups and combinations thereof;
   said polymer being a durable foam which is a reaction product of a reactant charge including: water, a polycarbonate glycol reactant having terminal hydroxyl groups, a diisocyanate reactant having terminal isocyanate groups, and a chain extender reactant having terminal hydroxyl or amine groups, wherein the polymer reaction product has a hardness in the range of about Shore 70A to about Shore 75D; and wherein said polymeric backbone includes:
   a linkage site at which at least one of said terminal isocyanate groups of a diisocyanate reactant moiety had reacted with at least one of said terminal hydroxyl groups of a polycarbonate glycol reactant moiety; and
   a linkage site at which another terminal isocyanate group of the diisocyanate reactant moiety had reacted with one of said terminal hydroxyl or amine groups of a polycarbonate glycol reactant moiety or a chain extender reactant moiety.

6. The polymer according to claim 2, wherein the polycarbonate urethane polymer is substantially devoid of ether linkages in excess of impurity or side reaction concentrations.

7. The polymer according to claim 1, wherein the polycarbonate urethane polymer has a molecular weight of between about 80,000 and about 200,000 Daltons.

8. The polymer according to claim 1, wherein said reactant charge further includes a polar organic solvent, and the crack-resistant products are fibers extruded from said reactant charge.

9. The polymer according to claim 1, wherein said polycarbonate urethane polymer further comprises a crack preventative composition bonded thereonto.

10. The polymer according to claim 9, wherein said crack preventative composition is an elastomeric silicone material.

11. A polycarbonate urethane polymer for forming crack-resistant implantable prostheses, the polymer comprising:
   a polymeric backbone having recurring groups selected from the group consisting of urethane groups, urea groups, carbonate groups and combinations thereof;
   said polymer being a reaction product of reactants including: a polycarbonate diol reactant having terminal hydroxyl groups, a diisocyanate reactant having terminal isocyanate groups, and a chain extender reactant having terminal hydroxyl or amine groups, wherein the polymer reaction product has a hardness of at least about Shore 70A or harder and the ratio of chain extender reactant terminal group equivalents to polycarbonate diol reactant terminal group equivalents is at least about 0.75 to 1 and not greater than about 12 to 1;
   wherein said polymeric backbone includes: a linkage site at which at least one of said terminal isocyanate groups of a diisocyanate reactant moiety had reacted with at least one of said terminal hydroxyl groups of a polycarbonate diol reactant moiety; and a linkage site at which another terminal isocyanate group of the diisocyanate reactant moiety had reacted with one of said terminal hydroxyl or amine groups of a polycarbonate diol reactant moiety or a chain extender reactant moiety; and
   said polymer is substantially devoid of ether linkages in excess of impurity or side reaction concentrations, whereby the prostheses are crack-resistant when implanted, and cracking of the polymer is substantially prevented during in vivo implantation for in excess of six months.

12. The polycarbonate urethane polymer according to claim 11, wherein said polycarbonate diol has a molecular weight of on the order of approximately 1000 Daltons, and said ratio of equivalents is between about 1 to 1 and about 3 to 1.

13. The polycarbonate urethane polymer according to claim 11, wherein said polycarbonate diol has a molecular weight of on the order of approximately 2000 Daltons, and said ratio of equivalents is between about 2 to 1 and about 6 to 1.

14. A method of making and implanting a biocompatible prosthesis, implant and the like, comprising the steps of:
   polymerizing a reactant charge including a polycarbonate glycol reactant having terminal hydroxyl groups, a diisocyanate reactant having terminal isocyanate groups and a chain extender reactant having terminal hydroxyl or amine groups, said reactant charge having a ratio of chain extender equivalent groups to polycarbonate equivalent groups of at least about 0.75 to 1 in order to provide a polycarbonate urethane polymer;
   extruding or casting said polycarbonate urethane polymer in order to form a crack-resistant prosthesis, implant and the like; and
   implanting said crack-resistant prosthesis, implant and the like under in vivo implantation conditions whereby cracking of the polycarbonate urethane polymer is substantially prevented during in vivo implantation for in excess of six months.

15. The method according to claim 14, wherein said polymerizing step includes adding water to said reactant charge.

16. The method according to claim 14, wherein said polymerizing step includes incorporating a polar organic solvent to said reactant charge.

17. The method according to claim 16, wherein said polymerizing step includes adding water to said reactant charge.

18. The method according to claim 14, further including bonding an elastomeric silicone material to said prosthesis, implant and the like.

19. The polymer according to claim 1, wherein said polycarbonate glycol reactant is an aliphatic polycarbonate which is a reaction product of 1,6-hexanediol with ethylene carbonate.

20. The polymer according to claim 5, wherein said polycarbonate glycol reactant is an aliphatic polycarbonate which is a reaction product of 1,6-hexanediol with ethylene carbonate.

21. The polycarbonate urethane polymer according to claim 11, wherein said polycarbonate diol reactant is an aliphatic polycarbonate which is a reaction product of 1,6-hexanediol with ethylene carbonate.

22. The method according to claim 14, wherein the polycarbonate glycol reactant of said polymerizing step is an aliphatic polycarbonate which is a reaction product of 1,6-hexandiol with ethylene carbonate.

23. A non-biodegradable urethane polymer, said polymer is a reaction product of a reactant charge including:
a macroglycol reactant having a molecular weight of between 200 and 4000 represented by the general formula:

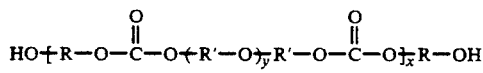

wherein x is from 2 to 35; y is 0, 1 or 2, wherein R is aliphatic, aromatic or cycloaliphatic having from about 4 to about 40 carbon atoms or is alkoxy having from about 2 to about 20 carbon atoms, and wherein R' has from about 2 to about 4 linear carbon atoms;
a diisocyanate reactant having terminal isocyanate groups; and
a chain extender reactant selected from at least one of water, diols, or diamines, wherein the polymer reaction product has a hardness equal to or greater than Shore 70A;
wherein the ratio of equivalents of said diisocyanate reactant to said macroglycol and chain extender reactants in total is on the order of approximately 1 to 1, and the ratio of equivalents of said chain extender to said macroglycol is between about 0.75 to 1 and about 12 to 1.

24. The non-biodegradable urethane polymer according to claim 23, wherein the polymer has a molecular weight of at least about 80,000 Daltons, measured by the polystyrene standard.

25. The non-biodegradable urethane polymer according to claim 23, wherein the viscosity of the polymer at a solids content of 43% is between about 900,000 and about 1,800,000 centipoise.

26. Crack-resistant biocompatible articles of manufacture of a non-biodegradable polycarbonate urethane polymer, the polymer comprising:
a polymeric backbone having recurring groups selected from the group consisting of urethane groups, urea groups, carbonate groups and combinations thereof;
said polymer being a reaction product of a reactant charge including: a polycarbonate glycol reactant having terminal hydroxyl groups, a diisocyanate reactant having terminal isocyanate groups, and a chain extender reactant having terminal hydroxyl or amine groups, wherein the polymer reaction product has a hardness in the range of about Shore 70 A or harder; wherein said polymeric backbone includes:
a linkage site at which at least one of said terminal isocyanate groups of a diisocyanate reactant moiety had reacted with at least one of said terminal hydroxyl groups of a polycarbonate glycol reactant moiety;
a linkage site at which another terminal isocyanate group of the diisocyanate reactant moiety had reacted with one of said terminal hydroxyl or amine groups of a polycarbonate glycol reactant moiety or a chain extender reactant moiety; and
said polymer is substantially devoid of ether linkages, whereby the biocompatible articles are crack-resistant so that cracking of the polymer is substantially prevented.

27. The articles according to claim 26, wherein the ratio of equivalents of chain extender to polycarbonate glycol is at least about 1.5 to 1.

28. The articles according to claim 27, wherein said ratio of equivalents is between about 2 to 1 and about 4 to 1.

29. The articles according to claim 26, wherein said polycarbonate glycol has a molecular weight of on the order of approximately 1000 Daltons, and the ratio of equivalents of chain extender to polycarbonate glycol is between about 1 to 1 and about 3 to 1.

30. The articles according to claim 26, wherein said polycarbonate glycol has a molecular weight of on the order of approximately 2000 Daltons, and the ratio of equivalents of chain extender to polycarbonate glycol is at least about 2 to 1.

31. The articles according to claim 26, wherein the polycarbonate urethane polymer is substantially devoid of ether linkages in excess of impurity of side reaction concentrations.

32. The articles according to claim 26, wherein the polycarbonate urethane polymer has a molecular weight of at least about 80,000 Daltons.

33. The articles according to claim 26, wherein said hardness is between about Shore 80 A and about Shore 75 D.

34. The articles according to claim 26, wherein the ratio of chain extender reactant terminal group equivalents to polycarbonate diol reactant terminal group equivalents is at least about 0.75 to 1 and not greater than about 12 to 1.

35. The articles according to claim 26, wherein said polycarbonate glycol reactant is an aliphatic polycarbonate which is a reaction product of 1,6-hexanediol with ethylene carbonate.

36. The articles according to claim 26, wherein said article is an extrusion or molding of said polycarbonate urethane polymer.

37. A method of making and using a biocompatible article, comprising the steps of:
polymerizing a reactant charge including a polycarbonate glycol reactant having terminal hydroxyl groups, a diisocyanate reactant having terminal isocyanate groups and a chain extender reactant having terminal hydroxyl or amine groups, said reactant charge having a ratio of chain extender equivalent groups to polycarbonate equivalent groups of at least about 0.75 to 1 in order to provide a polycarbonate urethane polymer;
extruding, molding or casting said polycarbonate urethane polymer in order to form a crack-resistant biocompatible article; and
using said crack-resistant biocompatible article under in vivo conditions whereby cracking of the polycarbonate urethane polymer is substantially prevented during said in vivo use.

38. The method according to claim 37, wherein the polycarbonate glycol reactant of said polymerizing step is an aliphatic polycarbonate which is a reaction product of 1,6-hexanediol with ethylene carbonate.

* * * * *

UNITED STATES PATENT AND TRADEMARK OFFICE
CERTIFICATE OF CORRECTION

PATENT NO. : 5,229,431
DATED : July 20, 1993
INVENTOR(S) : Leonard Pinchuk

It is certified that error appears in the above-indentified patent and that said Letters Patent is hereby corrected as shown below:

Title page:
In the Abstract of the Disclosure, line 3, replace "prosthesis" with --prostheses--.
Col. 1, line 7, "Ser. No. 749,621" should read --Ser. No. 794,621--; line 14, replace "prosthesis" with --prostheses--; line 50, replace "inhibition" with --imbibition--.
Col. 2, line 67, " would especially" should read --would be especially--.
Col. 5, line 7, replace "polycarvonate" with --polycarbonate--.
Col. 6, lines 9-10, "4,4-methylene" should read --4,4'-methylene--; line 15, replace "4,4'tolidine" with --4,4'-toluidine--; line 34, replace "heteromoleculs" with --heteromolecules--.
Col. 8, line 38, "1,4-butane diol" should read --1,4-butanediol--.

Signed and Sealed this

Fourth Day of July, 1995

Attest:

BRUCE LEHMAN

*Attesting Officer*     *Commissioner of Patents and Trademarks*